United States Patent [19]

Matsuo et al.

[11] Patent Number: 4,656,158
[45] Date of Patent: Apr. 7, 1987

[54] PEPTIDE, AND PRODUCTION AND USE THEREOF

[75] Inventors: Hisayuki Matsuo, 6653, Ooaza-Kihara, Kiyotake-cho, Miyazaki-gun, Miyazaki-ken; Kenji Kangawa, Miyazaki, both of Japan

[73] Assignees: Suntory Limited; Hisayuki Matsuo, both of Japan

[21] Appl. No.: 706,382

[22] Filed: Feb. 27, 1985

[30] Foreign Application Priority Data

Mar. 2, 1984 [JP] Japan .................. 59-38817

[51] Int. Cl.$^4$ ............ A61K 37/02; C07K 7/10; C07K 3/24
[52] U.S. Cl. ............................. 514/12; 530/324; 530/344
[58] Field of Search ............ 260/112.5 R; 514/12; 530/324, 344

[56] References Cited

PUBLICATIONS

Jamieson, J. D. and Palade, G. E., "Specific Granules in Atrial Muscle Cells", The Journal of Cell Biology, vol. 23, (1964), pp. 151–172.

de Bold, A. J. et al, "A Rapid and Potent Natriuretic Response to Intravenous Injection of Atrial Myocardial Extract in Rats", Life Sciences, vol. 28, (1981), pp. 89–94.

Keeler, R., "Atrial Natrieuretic Factor has a Direct, Prosteglan–Independent Action on Kidneys", Can. J. Physiol. Pharmacol, vol. 60, (1982), pp. 1078–1082.

Currie, M. G. et al, "Bioactive Cardiac Substances: Potent Vasorelaxant Activity in Mammalian Atria", Science, vol. 221, (1983), pp. 71–73.

Flynn, T. G. et al, "The Amino Acid Sequence of an Atrial Peptide with Potent Diuretic and Natriuretic Properties", Biochemical and Biophysical Research ...

Kanagawa, K. and Matsuo, H., "Purification and Complete Amino Acid Sequence of α-Human Atrial Natriuretic Polypeptide, (α-haNP)" Biochemical and Biophysical ....

Primary Examiner—Delbert R. Phillips
Attorney, Agent, or Firm—Burns, Doane, Swecker & Mathis

[57] ABSTRACT

There are disclosed a new peptide β-hANP of the following structure:

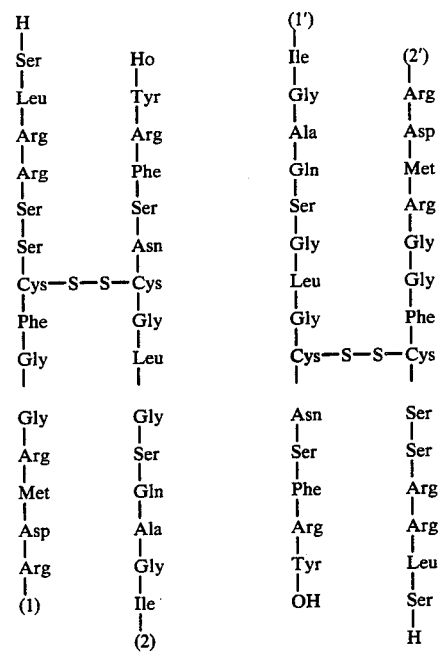

and acid addition salt thereof; a diuretic composition and a hypotensor composition containing a β-hANP or an acid addition salt thereof; and processes for the production thereof.

17 Claims, 2 Drawing Figures

PEPTIDE, AND PRODUCTION AND USE THEREOF

BACKGROUND OF THE INVENTION

1. Field of the Invention

The present invention relates to a novel peptide, a process for the production thereof, and a pharmaceutical composition containing the novel peptide as a diuretic or hypotensor.

2. Description of the Related Art

A normal regulation of the blood pressure in a human body is important for the maintenance of personal health, and various physical and humoral factors contribute to this regulation of the blood pressure. The physical factors include, for example, output, and the elasticity of the walls of blood vessels, etc. The humoral factors include, for example, the renin-angiotensin-aldosterone system, catecholamines, prostaglandins, kinin-kallikrein system, and natriuretic hormones including ouabain-like substances. Herein the term "natriuretic" will denote selective excretion of sodium cation relating to potassium cation.

Granules morphologically similar to granules present in peptide hormone-producing cells are found in human atrium (J. D. Jamieson and G. E. Palade, *J. Cell Biol.*, 23, 151, 1964). A homogenate of rat atrium and granules contained therein are known to show natriuretic action in rats (A. J. DeBold et. al., *Life Science*, 28, 89, 1981; R. Keeler, *Can. J. Physiol. Pharmacol.*, 60, 1078, 1982). Recently Mark G. Currie et. al. suggested peptide-like substances with a molecular weight of 20,000 to 30,000 or not more than 10,000, present in atrium of humans, rabbits, swine, and rats, and having natriuretic action (*Science*, 221, 71–73, 1983).

Moreover, a peptide consisting of 28 amino acids derived from rat atrium cordis was identified (*Biochem. Biophys. Res. Commun.*, Vol. 117, No. 3, p859–865, 1983). The present inventors found a new peptide consisting of 28 amino acids from human atrium cordis; referred to as "α-human atrial natriuretic polypeptide" and abbreviated as "α-hANP" (*Biochem. Biophys. Res. Commun.*) Vol. 118, No. 1, p131–139, 1984).

SUMMARY OF THE INVENTION

The present invention provides a new peptide having natriuretic action and hypotensive or antihypertensive action. The peptide according to the present invention is hereinafter referred to as "β-human atrial natriuretic polypeptide" and abbreviated as "β-hANP".

There is also provided a process for production of the peptide.

Another object of the present invention is to provide a pharmaceutical composition containing the peptide as a diuretic or hypotensor.

Other objects and advantages of the present invention will be apparent from the description set forth hereinbelow.

DESCRIPTION OF THE PREFERRED EMBODIMENT

Figure 1:
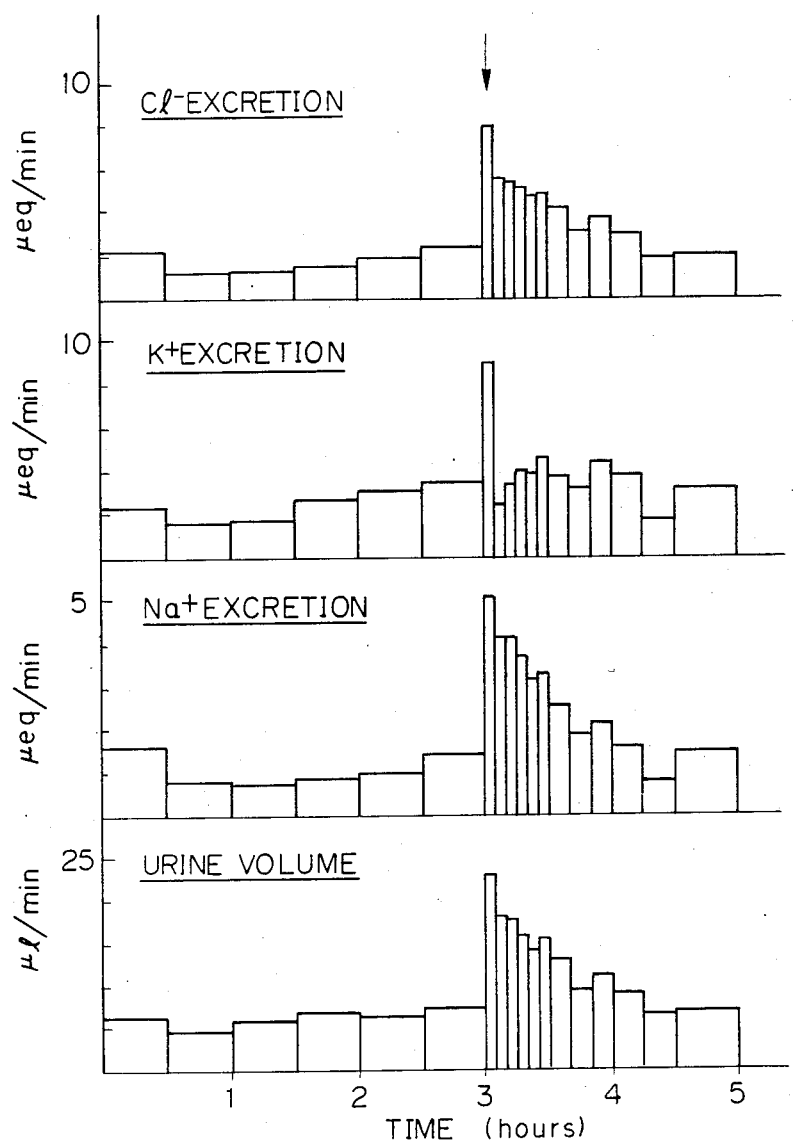
FIG. 1 contains graphs showing the diuretic and natriuretic action of the β-hANP.

At present, furosemide as a natriuretic agent is used for the treatment of essential hypertension. However, the structure of the furosemide is different to that of the new peptide according to the present invention.

The present inventors isolated a peptide, in substantially pure form, consisting of 56 amino acid residues and having a molecular weight of about 6,000, determined the structure of the peptide and found that the peptide showed notable natriuretic and hypotensive action.

Structure and Physico-chemical Properties of the β-hANP (1) Structure

The β-hANP has the structure:

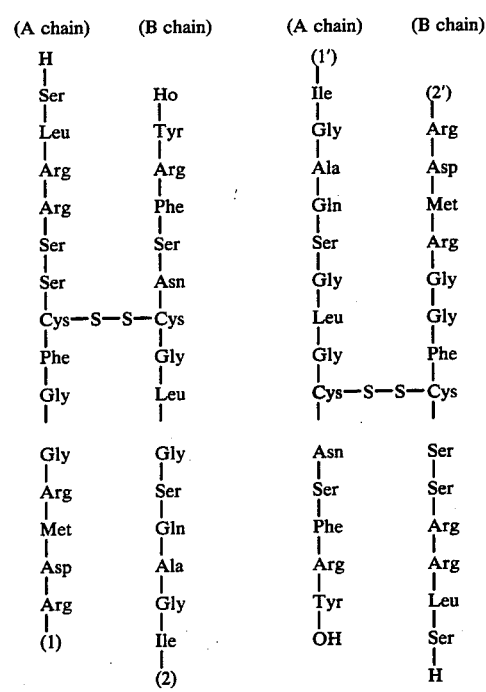

wherein (1) and (1'), and (2) and (2') are directly bonded; Asp represents L-aspartic acid, Asn represents L-asparagine, Ala represents L-alanine, Arg represents L-arginine, Ile represents L-isoleucine, Gly represents glycine, Gln represents L-glutamine, Cys represents together with —S— ½ L-cystine, Ser represents L-serine, Tyr represents L-tyrosine, Phe represents L-phenylalanine, Met represents L-methionine, and Leu represents L-leucine; and the peptide chain A has an amino-terminal at the left end and a carboxy-terminal at the right end, and the peptide chain B has an amino-terminal at the right end and a carboxy-terminal at the left end.

(2) Molecular weight: about 6,000 as determined by gel-filtration (6160.78 as calculated).

(3) UV spectrum: Max=275 mm.

(4) Color reactions: Ehrlich's reaction, negative; Sakaguchi's reaction, positive; Pauly's reaction, positive.

(5) Distinction of basic, acidic, or neutral property: basic.

(6) Solubility in solvents: soluble in water, partially in methanol, and acetic acid; insoluble in ethyl acetate, butyl acetate, ethyl ether, hexane, petroleum ether, benzene, and chloroform.

(7) Amino acid composition by amino acid analysis:

| Amino acid | β-hANP | | RCM β-hANP* | |
|---|---|---|---|---|
| | Found | Calculated | Found | Calculated |
| Asp + Asn | 4.14 | 4 | 2.08 | 2 |
| Ala | 2.06 | 2 | 1.05 | 1 |
| Arg | 9.90 | 10 | 5.02 | 5 |
| Ile | 1.94 | 2 | 0.97 | 1 |
| Gly | 10.00 | 10 | 5.03 | 5 |
| Glu(Gln) | 2.06 | 2 | 1.01 | 1 |
| (Cys)$_2$ | | 2 | 0.99 | 1 |
| Ser | 10.18 | 10 | 5.17 | 5 |
| Tyr | 1.92 | 2 | 1.03 | 1 |
| Phe | 4.16 | 4 | 2.09 | 2 |
| Met | 2.18 | 2 | 0.95 | 1 |
| Leu | 3.98 | 4 | 2.06 | 2 |

(8) Determination of the structure

A product obtained after reduction of β-hANP with dithiothreitol to cleave a disulfide bond of the β-hANP and subsequent carboxymethylation of the cleft product, and that obtained from α-hANP by the same procedure provided an identical elution pattern showing a single peak in a liquid chromotography. These carboxymethylated products were digested with trypsin, and each digestion product was subjected to a liquid chromatography. In the chromatography, the digestion products from α-hANP and β-hANP provided an identical elution pattern, i.e., an identical combination of the digestion fragments. Moreover, a molecular weight of β-hANP was about two times that of α-hANP. These facts show that the β-hANP is a dimer of the α-hANP wherein the two α-hANP molecules are bonded through two disulfide bonds.

β-hANP and α-hANP were digested with trypsin, and the digestion products were analyzed by liquid chromatography for the fragment composition. A comparison of the fragment compositions from β-hANP and α-hANP showed that, in the β-hANP, two α-hANP molecules which are directed in reverse to each other are bonded through two disulfide bonds.

(9) Formation of salts: the β-hANP is a basic compound as described in item (5), and can form acid addition salts with an inorganic acid such as hydrochloric acid, sulfuric acid, phosphoric acid, or an organic acid such as formic acid, acetic acid, propionic acid, succinic acid, and citric acid.

Physiological Properties of β-hANP

The β-hANP according to the present invention has notable diuretic, natriuretic, and hypotensive or antihypertensive actions.

Test method:

Male rats weighing 300 to 400 grams were anesthetized by intraperitoneal administration of pentobarbital at a dosage of 60 mg/kg, and used for tests of the β-hANP according to the method described in *Life Sciences*, Vol. 28, pp89–94.

To keep the respiratory tract open, a tracheal cannula (PE240 Clay-Adams) was inserted into the trachea. An arterial cannula (PE-50) was inserted into a femoral artery for measurement of the blood pressure, and a venous cannula was inserted into a femoral vein for the administration of Ringer's solution. 1.2 ml of Ringer's solution was infused at a flow rate of 1.2 ml/hour.

A bladder cannula made of silastic tube with a inner diameter of 0.02 inches and an outer diameter of 0.037 inches was inserted into the bladder, and via the cannula, a urine sample was collected into a test tube. The collection of urine was carried out for 30 minutes before administration of the test compound, and every five minutes after the administration.

0.8 n mole of the test compound β-hANP was dissolved in 50 μl of sterilized physiological saline with 5 μg of bacitracin, and the solution was injected into the jugular vein.

The results of the test are set forth in FIG. 1. As shown in the figure, β-hANP shows notable diuretic and natriuretic actions. The actions of β-hANP are comparable to those of α-hANP, but are maintained for a period longer than that of α-hANP. 0.8 n mole of β-hANP provides diuretic and natriuretic actions comparable to those provided by 1.21 μ mole of furosemide, which is a known diuretic agent. However, β-hANP brings about the actions more rapidly than furosemide.

Use of β-hANP as a pharmaceutical product

Repeated administration of β-hANP does not stimulate production of antibodies, and does not cause anaphylaxis shock. β-hANP consisting of L-amino acids is gradually hydrolized in a body providing the L-amino acids, and therefore shows little toxicity.

Due to the higher diuretic, natriuretic, and blood pressure-lowering or antihypertensive actions, and the lower toxicity, β-hANP is useful as an active ingredient for pharmaceutical compositions such as a diuretic and a hypotensor. β-hANP is administered at 0.1 μg/kg to 1 mg/kg, preferably 1 μg/kg to 100 μg/kg.

β-hANP can be administered in the same manner as conventional peptide type pharmaceuticals. Namely, β-hANP is preferably administered parenterally, for example, intravenously, intramuscularly, intraperitoneally, or subcutaneously. β-hANP, when administered orally, may be proteolytically hydrolyzed. Therefore, oral application is not usually effective. However, β-hANP can be administered orally as a formulation wherein β-hANP is not easily hydrolyzed in a digestive tract, such as liposome-microcapsules. β-hANP may be also administered in suppositories, sublingual tablets, or intranasal spray.

The parenterally administered pharmaceutical composition is an aqueous solution containing about 0.000005 to 5%, preferably 0.00005 to 0.5% of β-hANP, which may contain, in addition to β-hANP as an active ingredient, for example, buffers such as phosphate, acetate, etc., osmotic pressure-adjusting agents such as sodium chloride, sucrose, and sorbitol, etc., antioxidative or antioxygenic agents, such as ascorbic acid or tocopherol and preservatives, such as antibiotics. The parenterally administered composition also may be a solution readily usable or in a lyophilized form which is dissolved in sterile water before administration.

Production of β-hANP

β-hANP can be produced by either the extraction of the β-hANP from human atrium or by chemical synthesis.

In the former process, human atrium is homogenized in an acidic aqueous solution such as a phosphate buffer solution, or an acetic acid solution containing hydrochloric acid. Subsequently, β-hANP is purified according to a conventional method suitable for the purification of peptide, such as centrifugation, isoelectric point precipitation, solvent extraction, ultrafiltration, gel filtration, adsorption chromatography or high performance liquid chromatography (HPCL), or a combination of such methods. In the above-mentioned methods, chick rectum relaxation activity is conveniently used to select fractions containing β-hANP, because β-hANP has this activity. In the chromatography methods, the β-hANP containing fractions can be also selected by molecular weight (about 5,000 to 6,000). Chemical synthesis is preferable for the industrial production of β-hANP, in which chemical synthesis, a liquid phase method or solid phase method, or a combination thereof can be used. The solid phase method such as Merrifield's method [R. B. Merrifield, J. Am. Chem. Soc. 85, 2184 (1963)] is most convenient.

In Merrifield's method, each amino acid is protected preferably with tert-butyloxycarbonyl (Boc) at the α-amino group; a hydroxyl group in tyrosine is protected preferably with 2,6-dichlorobenzyl group ($Cl_2Bzl$); a guanidino group in arginine is protected preferably with a tosyl group (Tos); a hydroxyl group in serine is protected preferably with a benzyl group (Bzl); a β-carboxyl group in aspartic acid is protected preferably with an O-benzyl group (O-Bzl); and a thiol group in cysteine is protected with an acetoamidomethyl group (Acm). In the Merrifield method, first a protected derivative of C-terminal amino acid L-tyrosin, i.e., Boc-Tyr ($Cl_2Bzl$), is introduced onto a solid phase resin carrier, such as chloromethyl-resin, and subsequently, each suitably protected amino acid is coupled to a terminal amino acid of an intermediate amino acid chain bonded to the resin, in the order of the amino acid sequence of α-hANP. After all the amino acids are coupled in the predetermined order, the protected α-hANP thus obtained is removed from the resin by treatment with hydrogen fluoride, and simultaneously protecting groups other than Acm are also removed. The product is then reduced to obtain $Cys^{7,23}$(Acm)-α-hANP), which is then oxidized with iodine to remove the thiol-protecting group Acm, and simultaneously, to form a disulfide bond. The crude-β-hANP thus obtained is then purified by conventional methods such as gel filtration, reverse phase HPLC, etc., to obtain purified β-hANP.

EXAMPLES

The present invention will now be further illustrated by, but is by no means limited to, the following examples.

EXAMPLE 1

Preparation of β-hANP from human atrium cordis

Ten hours after death, 40 g of human atrium cordis was removed and boiled in seven volumes of 1M acetic acid aqueous solution containing 20 mM hydrochloric acid for five minutes, to inactivate protease present in the atrium cordis. The boiled atrium cordis in the acetic acid solution was then cooled to 4° C., and homogenized with a Polytron homogenizer to extract the β-hANP. The homogenate thus obtained was centrifuged at 12000 XG for 30 minutes to obtain 200 ml of a supernatant. To the supernatant, 12 ml of glacial acetic acid was added to the concentration of 1M acetic acid, and acetone was dropwise added in an amount of 66% of the final concentration to precipitate impurities. The mixture thus obtained was centrifuged to obtain 424 ml of supernatant containing β-hANP, which was then evaporated to dryness. The residue thus obtained was dissolved in 100 ml of 1N acetic acid, and the solution was extracted two times with 50 ml of ethyl ether to defat the solution. The aqueous phase thus obtained was lyophilized, and the lyophilizate was redissolved in 100 ml of 1N acetic acid. The solution was then ultrafiltrated with a UM-2 filter (Amicon) to desalt the solution. The desalted solution was concentrated to 50 ml.

The concentrated solution was applied on SP-Sephadex C-25 column (Pharmacia, 8.0×22 cm). The elution was carried out with 1N acetic acid, 2N pyridine solution, aND 2N pyridine-1N acetic acid solution (pH 5.0), in that order, to obtain fractions SP-I, SP-II, and SP-III. The fraction SP-III was lyophilized to obtain 26.6 mg of lyophilizate, which was then dissolved in 1N acetic acid.

Figure 2:
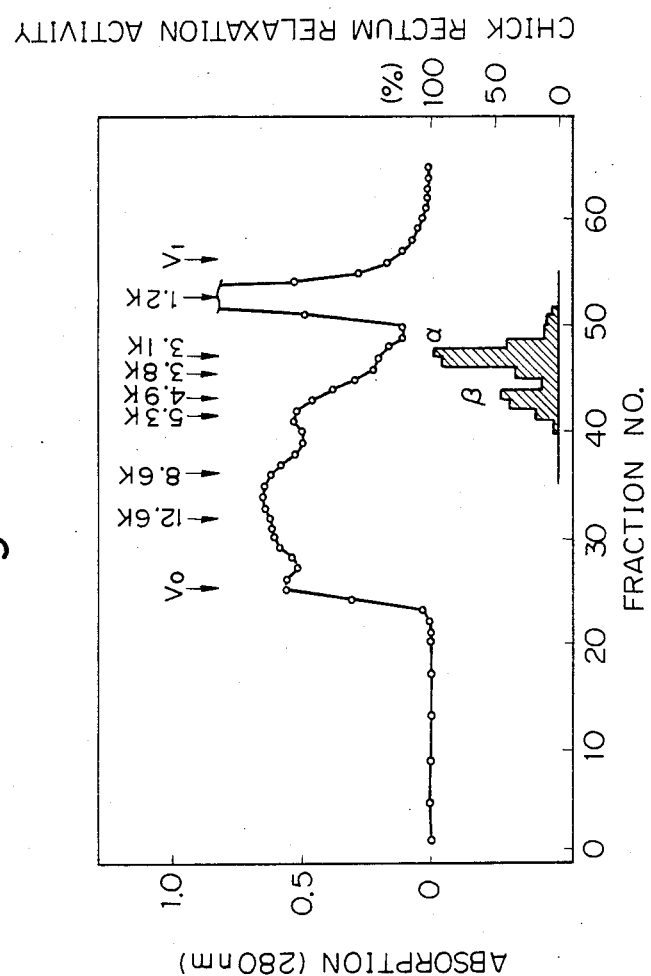
FIG. 2 is a chromatogram showing an elution profile wherein β-component is separated from α-component during isolation of β-hANP from human atrium cordis.

The solution thus obtained was gel-filtrated with Sephadex G-25 column (1.2×103 cm) at a flow rate of 5.4 ml/hour, collecting 2 ml of fractions. Thereby, β fractions (fractions No. 42 to 45) which have chick rectum relaxation activity were obtained. The elution profile is shown in FIG. 2. The β fractions were combined for further purification.

The combined fraction was then subjected to cation exchange HPLC in a TSK-CM2SW column (Toyo Soda, 7.5×300 mm). Elution was carried out by linear gradient with (A) 10 mM ammonium formate (pH 6.6)/acetonitrile (90:10) and (B) 1.0M ammonium formate (pH 6.6)/acetonitrile (90:10), after (A) for 12 minutes, changing the concentration of formate from 10 mM to 0.75M for 140 minutes. A set of fractions (No. 66 and 67, retention time 140 to 142 minutes) with chick rectum relaxation activity was obtained. The active fractions were combined and subjected to reverse phase HPLC in a TSK LS-410 ODS-SIL column (φ4.0×250 mm, Toyo Soda). Elution was carried out with (A) water/acetonitrile/10% trifluoroacetic acid (90:10:1) and (B) water/acetonitrile/10% trifluoroacetic acid (40:60:1) as eluents wherein the eluent (A) was used for 15 minutes and then linear gradient from (A) to (B) was used for 80 minutes, at a flow rate of 1.0 ml/min., and pressure of 110 to 130 kg/cm². A main peak was collected and 11 n mole of substantially pure β-hANP was obtained.

EXAMPLE 3

Preparation of parenteral composition (A) Injection solution

| Composition | |
|---|---|
| β-hANP | 2 g |
| sodium chloride | 8 g |
| ascorbic acid | 2 g |
| sterile water | 1 l |

Method

β-hANP and sodium chloride were dissolved in sterile water, an ampule was filled with 5 ml of the solution, and the ampule was then sealed.

(B) Lyophilizate

| Composition | |
|---|---|
| β-hANP | 2 g |

| Composition | |
|---|---|
| sorbitol | 20 g |

Method

β-hANP and sorbitol were dissolved in 200 ml of sterile water, a vial was filled with 1 ml of the solution, and lyophilized, and the vial was then sealed.

The composition is dissolved in 5 ml of sterile water before parenteral administration.

We claim:

1. A peptide β-hANP having the following formula:

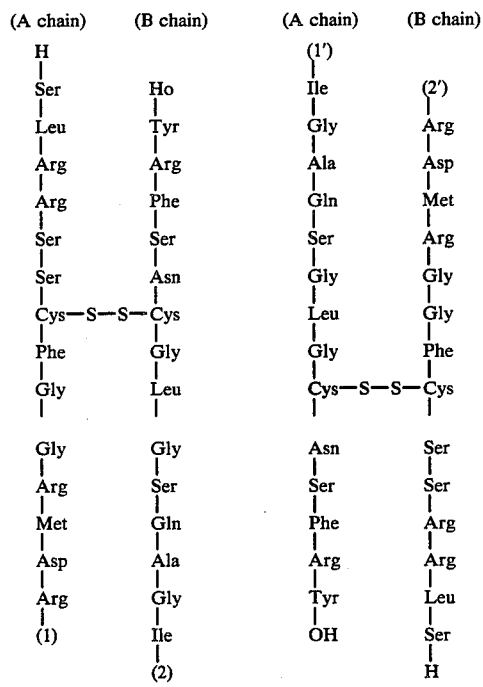

wherein (1) and (1'), are directly bonded and (2) and (2') are directly bonded; Asp represents L-aspartic acid, Asn represents L-asparagine, Ala represents L-alanine, Arg represents L-arginine, Ile represents L-isoleucine, Gly represents glycine, Gln represents L-glutamine, Cys represents together with —S— ½ L-cystine, Ser represents L-serine, Tyr represents L-tyrosine, Phe represents L-phenylalanine, Met represents L-methionine, and Leu represents L-leucine; and the peptide chain A has an amino-terminal at the left end and a carboxy-terminal at the right end, and the peptide chain B has an amino-terminal at the right end and a carboxy-terminal at the left end, or an acid addition salt thereof.

2. A pharmaceutical composition for use as a diuretic or antihypertensive agent comprising a diuretically effective amount or a blood pressure lowering effective amount of a peptide β-hANP according to claim 1 or an acid addition salt thereof with a conventional pharmaceutical additive.

3. The pharmaceutical composition according to claim 2, wherein the composition is a solution for parenteral administration and the conventional pharmaceutical additive is a buffer, an osmotic pressure adjusting agent or a preservative, or a combination thereof.

4. The pharmaceutical composition according to claim 2, wherein the composition is a solution for parenteral administration and contains about 0.000005 to 5% of the β-hANP.

5. The pharmaceutical composition according to claim 2, wherein the composition is in a lyophilized form.

6. A method for promoting diuresis comprising administering a composition comprising a diuretically effective amount of a peptide β-hANP having the following formula:

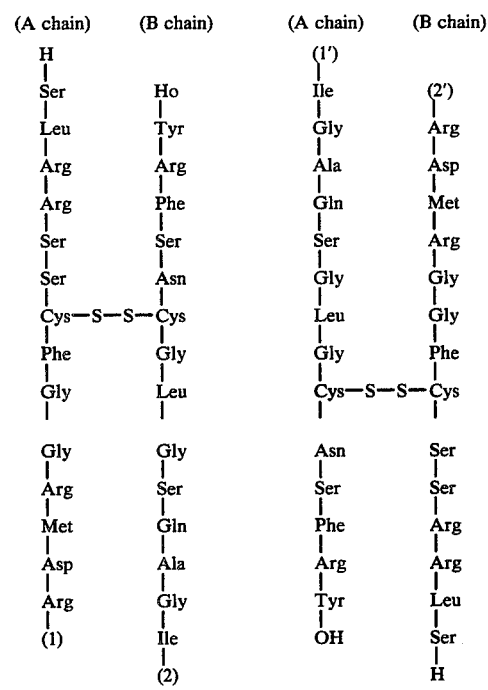

wherein (1) and (1') are directly bonded, and (2) and (2') are directly bonded; Asp represents L-aspartic acid, Asn represents L-asparagine, Ala represents L-alanine, Arg represents L-arginine, Ile represents L-isoleucine, Gly represents glycine, Gln represents L-glutamine, Cys represents together with —S— ½ L-cystine, Ser represents L-serine, Tyr represents L-tyrosine, Phe represents L-phenylalanine, Met represents L-methionine, and Leu represents L-leucine; and the peptide chain A has an amino-terminal at the left end and a carboxy-terminal at the right end, and the peptide chain B has an amino-terminal at the right end and a carboxy-terminal at the left end, or an addition salt thereof, with a conventional pharmaceutical additive.

7. The method according to claim 6, wherein the composition comprises about 0.000005 to 5% of the β-hANP.

8. The method according to claim 7, wherein the composition is administered parenterally.

9. The method according to claim 6, wherein the conventional pharmaceutical additive is a buffer, an osmotic pressure adjusting agent, a preservative or a combination thereof.

10. The method according to claim 6, wherein the composition is in lyophilized form.

11. A method for lowering blood pressure comprising administering an antihypertensively effective amount of a peptide β-hANP having the following formula:

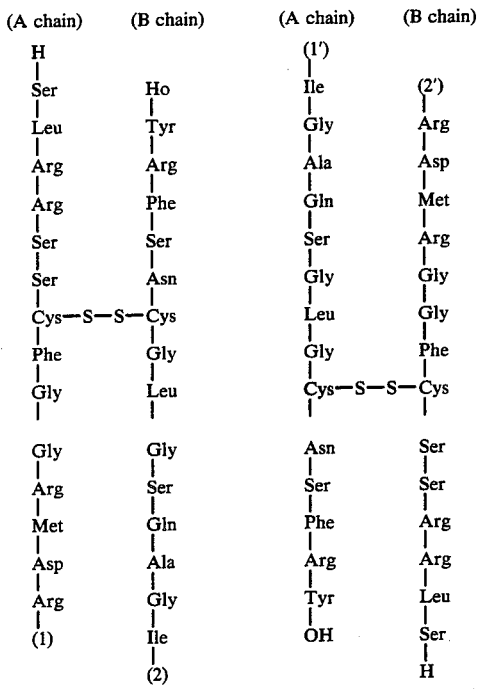

wherein (1) and (1') are directly bonded, and (2) and (2') are directly bonded; Asp represents L-aspartic acid, Asn represents L-asparagine, Ala represents L-alanine, Arg represents L-arginine, Ile represents L-isoleucine, Gly represents glycine, Gln represents L-glutamine, Cys represents together with —S— ½ L-cystine, Ser represents L-serine, Tyr represents L-tyrosine, Phe represents L-phenylalanine, Met represents L-methionine, and Leu represents L-leucine; and the peptide chain A has an amino-terminal at the left end and a carboxy-terminal at the right end, and the peptide chain B has an amino-terminal at the right end and a carboxy-terminal at the left end, or an addition salt thereof, with a conventional pharmaceutical additive.

12. The method according to claim 11, wherein the composition comprises about 0.000005 to 5% of the β-hANP.

13. The method according to claim 12, wherein the composition is administered parenterally.

14. The method according to claim 11, wherein the conventional pharmaceutical additive is a buffer, an osmotic pressure adjusting agent, a preservative or a combination thereof.

15. The method according to claim 11, wherein the composition is in lyophilized form.

16. A process for the production of a peptide β-hANP or an addition salt thereof according to claim 1 which comprises the following steps:
    (a) boiling rat atrium in an acidic solution;
    (b) homogenizing said rat atrium to obtain a homogenate;
    (c) centrifuging the homogenate to obtain a supernatant containing the β-hANP; and
    (d) separating said β-hANP from impurities using a purification process comprising organic solvent-precipitation, adsorption chromatography, ultrafiltration, gel filtration or high performance liquid chromatography to obtain said β-hANP in substantially purified form.

17. The process according to claim 16, further comprising the step (e) converting said β-hANP into an acid addition salt thereof or acid addition salt thereof or acid addition salt into free β-hANP.

* * * * *